(12) United States Patent
Wall

(10) Patent No.: US 11,564,812 B2
(45) Date of Patent: Jan. 31, 2023

(54) SURGICAL INSTRUMENT AND METHOD

(71) Applicant: Warsaw Orthopedic, Inc., Warsaw, IN (US)

(72) Inventor: Daniel Paxton Wall, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 358 days.

(21) Appl. No.: 16/564,722

(22) Filed: Sep. 9, 2019

(65) Prior Publication Data

US 2021/0068980 A1 Mar. 11, 2021

(51) Int. Cl.
| | | |
|---|---|---|
| *A61F 2/46* | (2006.01) | |
| *A61B 34/10* | (2016.01) | |
| *A61F 2/44* | (2006.01) | |
| *A61B 34/20* | (2016.01) | |
| *A61B 34/30* | (2016.01) | |

(52) U.S. Cl.
CPC ............ *A61F 2/4611* (2013.01); *A61B 34/10* (2016.02); *A61B 34/20* (2016.02); *A61F 2/44* (2013.01); *A61B 34/30* (2016.02); *A61B 2034/107* (2016.02); *A61B 2034/2051* (2016.02); *A61B 2034/2055* (2016.02); *A61F 2002/4632* (2013.01)

(58) Field of Classification Search
CPC . A61F 2/46; A61F 2/4611; A61F 2/44; A61B 34/10; A61B 34/20
See application file for complete search history.

(56) References Cited

U.S. PATENT DOCUMENTS

| | | | |
|---|---|---|---|
| 3,901,298 A | * | 8/1975 | Eby .................... B25B 23/10 81/125 |
| 4,423,721 A | | 1/1984 | Otte et al. |
| 4,612,918 A | | 9/1986 | Slocum |
| 4,773,402 A | | 9/1988 | Asher et al. |
| 4,961,740 A | | 10/1990 | Ray et al. |
| 5,026,373 A | | 6/1991 | Ray et al. |

(Continued)

FOREIGN PATENT DOCUMENTS

| | | |
|---|---|---|
| WO | 2015118543 A1 | 8/2015 |
| WO | 2015162612 A1 | 10/2015 |
| WO | 2016065489 A1 | 5/2016 |

OTHER PUBLICATIONS

International Search Report and Written Opinion of the International Searching Authority dated Dec. 14, 2020 in corresponding International PCT application No. PCT/US2020/049306 filed on Sep. 4, 2020.

*Primary Examiner* — Christopher J Beccia
(74) *Attorney, Agent, or Firm* — Sorell, Lenna & Schmidt, LLP

(57) ABSTRACT

A surgical instrument having a first member being engageable with a fastener. A second member includes an expandable portion configured for capturing the fastener. A third member is engageable with the expandable portion to releasably capture the fastener. An actuator connected with the second member and the third member. The actuator includes a threaded inner surface and a threaded coupling member engageable with the threaded inner surface to facilitate axial translation of the second member relative to the third member. Systems, spinal constructs, implants and methods are disclosed.

20 Claims, 16 Drawing Sheets

(56) References Cited

U.S. PATENT DOCUMENTS

| | | |
|---|---|---|
| 5,108,397 A | 4/1992 | White |
| 5,334,205 A | 8/1994 | Cain |
| 5,669,909 A | 9/1997 | Zdeblick et al. |
| 6,021,343 A | 2/2000 | Foley et al. |
| 6,030,162 A | 2/2000 | Huebner |
| 6,053,916 A | 4/2000 | Moore |
| 6,217,331 B1 | 4/2001 | Rogers et al. |
| 6,224,603 B1 | 5/2001 | Marino |
| 6,299,615 B1 | 10/2001 | Huebner |
| 6,635,059 B2 | 10/2003 | Randall et al. |
| 6,648,903 B1 | 11/2003 | Pierson, III |
| D484,596 S | 12/2003 | Ryan et al. |
| 6,755,835 B2 | 6/2004 | Schultheiss et al. |
| 6,964,665 B2 | 11/2005 | Thomas et al. |
| 6,981,974 B2 | 1/2006 | Berger |
| 7,174,812 B1 * | 2/2007 | Chiang .................. B25B 13/44 81/125 |
| 7,338,286 B2 | 3/2008 | Porter et al. |
| 7,354,442 B2 | 4/2008 | Sasso et al. |
| D574,495 S | 8/2008 | Petersen |
| 7,473,256 B2 | 1/2009 | Assell et al. |
| 7,491,236 B2 | 2/2009 | Cragg et al. |
| 7,527,611 B2 | 5/2009 | Sweeney |
| 7,575,572 B2 | 8/2009 | Sweeney |
| 7,582,107 B2 | 9/2009 | Trail et al. |
| 7,597,557 B2 | 10/2009 | Fromovich et al. |
| 7,625,395 B2 | 12/2009 | Muckter |
| 7,637,954 B2 | 12/2009 | Michelson |
| 7,648,509 B2 | 1/2010 | Stark |
| 7,766,917 B2 | 8/2010 | Kugler et al. |
| 7,806,693 B2 | 10/2010 | Hurson |
| 7,827,694 B2 | 11/2010 | Soler et al. |
| 7,845,945 B2 | 12/2010 | Canter |
| 7,862,587 B2 | 1/2011 | Jackson |
| 7,905,908 B2 | 3/2011 | Cragg et al. |
| D643,921 S | 8/2011 | Davila |
| 8,038,442 B2 | 10/2011 | Hurson |
| 8,394,108 B2 | 3/2013 | McLean et al. |
| 8,394,132 B2 | 3/2013 | Lewis et al. |
| 8,460,307 B2 | 6/2013 | Saidha et al. |
| 8,574,273 B2 | 11/2013 | Russell et al. |
| D696,466 S | 12/2013 | Silva |
| D700,322 S | 2/2014 | Kleiner |
| 8,747,472 B2 | 6/2014 | Ainsworth et al. |
| 8,758,012 B2 | 6/2014 | Hurson |
| 8,777,960 B2 * | 7/2014 | Murray ............... A61B 17/8888 606/104 |
| 8,784,431 B1 | 7/2014 | Harder et al. |
| 8,932,059 B2 | 1/2015 | Dukhan |
| 8,932,303 B2 | 1/2015 | Bouliane |
| 8,968,372 B2 | 3/2015 | Biedermann et al. |
| 8,974,932 B2 | 3/2015 | McGahan et al. |
| 8,986,348 B2 | 3/2015 | Reiley |
| 9,095,397 B2 | 8/2015 | Kremer et al. |
| 9,113,972 B2 | 8/2015 | Trudeau |
| 9,119,685 B2 | 9/2015 | Butler et al. |
| 9,173,042 B2 | 10/2015 | Jinton et al. |
| 9,364,299 B2 | 6/2016 | Marlin |
| 9,451,999 B2 | 9/2016 | Simpson et al. |
| 2002/0049447 A1 | 4/2002 | Li |
| 2002/0198527 A1 | 12/2002 | Muckter |
| 2004/0038179 A1 | 2/2004 | Kumar et al. |
| 2004/0138662 A1 | 7/2004 | Landry et al. |
| 2006/0106382 A1 | 5/2006 | Gournay et al. |
| 2006/0161154 A1 | 7/2006 | McAfee |
| 2006/0161261 A1 | 7/2006 | Brown et al. |
| 2007/0027543 A1 | 2/2007 | Gimble et al. |
| 2007/0265621 A1 | 11/2007 | Matthis et al. |
| 2007/0270879 A1 | 11/2007 | Isaza et al. |
| 2008/0021454 A1 | 1/2008 | Chao et al. |
| 2008/0021456 A1 | 1/2008 | Gupta et al. |
| 2008/0039843 A1 | 2/2008 | Abdou |
| 2008/0140082 A1 | 6/2008 | Erdem et al. |
| 2009/0018660 A1 | 1/2009 | Roush |
| 2009/0024174 A1 | 1/2009 | Stark |
| 2009/0099610 A1 | 4/2009 | Johnson et al. |
| 2009/0216238 A1 | 8/2009 | Stark |
| 2009/0259261 A1 | 10/2009 | Reiley |
| 2009/0326545 A1 * | 12/2009 | Schaffhausen ..... A61B 17/8891 81/436 |
| 2010/0010496 A1 | 1/2010 | Isaza et al. |
| 2010/0042164 A1 | 2/2010 | Lee et al. |
| 2010/0087878 A1 | 4/2010 | Abdou |
| 2010/0094290 A1 | 4/2010 | Vaidya |
| 2010/0106200 A1 | 4/2010 | Stark |
| 2010/0131011 A1 | 5/2010 | Stark |
| 2010/0298838 A1 | 11/2010 | Walters |
| 2012/0095515 A1 | 4/2012 | Hamilton |
| 2013/0004916 A1 | 1/2013 | Bellanca et al. |
| 2013/0022942 A1 | 1/2013 | Zadeh |
| 2013/0090696 A1 | 4/2013 | Chiquillo Perez |
| 2013/0144344 A1 | 6/2013 | Giancola |
| 2013/0282019 A1 * | 10/2013 | Bouliane ............. A61B 17/888 606/104 |
| 2014/0012340 A1 | 1/2014 | Beck et al. |
| 2014/0031872 A1 | 1/2014 | Jackson |
| 2014/0046381 A1 | 2/2014 | Asfora |
| 2014/0100616 A1 | 4/2014 | Shipp |
| 2014/0222087 A1 | 8/2014 | Greenberg et al. |
| 2014/0257408 A1 | 9/2014 | Trieu et al. |
| 2014/0303676 A1 | 10/2014 | Stroncek et al. |
| 2015/0105833 A1 | 4/2015 | Simpson et al. |
| 2015/0182309 A1 | 7/2015 | Soler et al. |
| 2015/0238305 A1 | 8/2015 | Meade et al. |
| 2016/0015483 A1 | 1/2016 | Kumar et al. |
| 2016/0120627 A1 | 5/2016 | Gil Mur et al. |
| 2016/0262809 A1 | 9/2016 | May et al. |
| 2016/0262819 A1 | 9/2016 | May et al. |
| 2016/0310188 A1 | 10/2016 | Marino et al. |
| 2018/0014863 A1 | 1/2018 | Biester et al. |
| 2019/0029737 A1 | 1/2019 | Wall et al. |

* cited by examiner

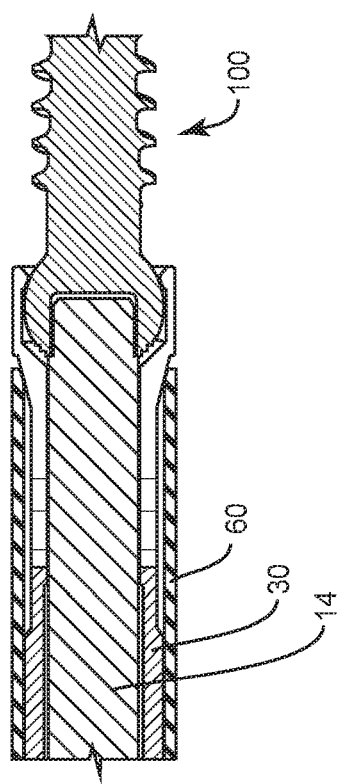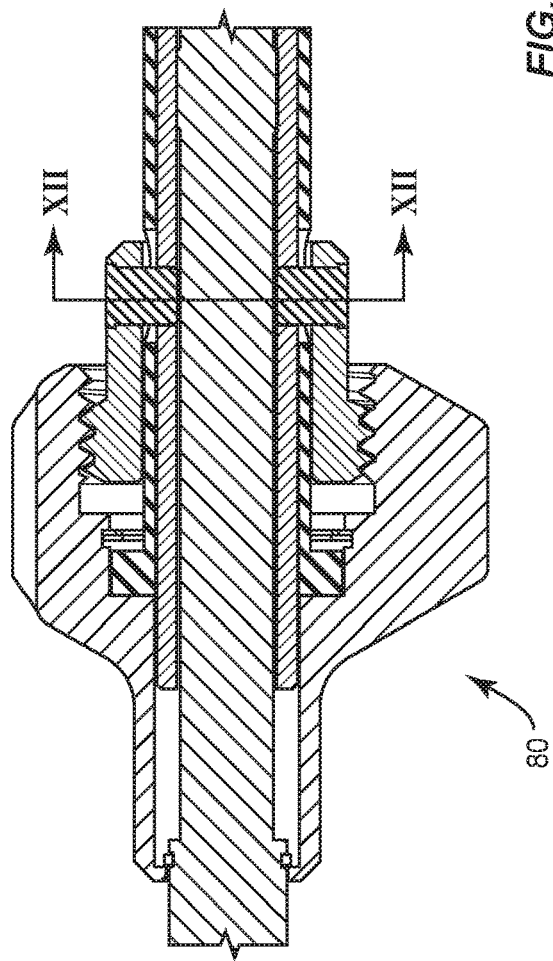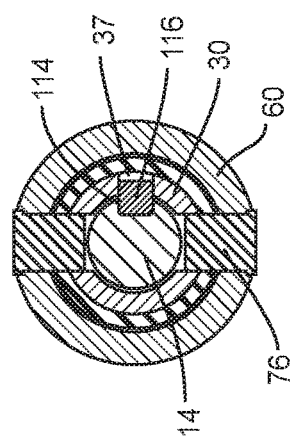
FIG. 11
FIG. 12

SURGICAL INSTRUMENT AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument includes a first member engageable with a fastener. A second member includes an expandable portion configured for capturing the fastener. A third member is engageable with the expandable portion to releasably capture the fastener. An actuator is connected with the second member and the third member. The actuator includes a threaded inner surface and a threaded coupling member engageable with the threaded inner surface to facilitate axial translation of the second member relative to the third member. In some embodiments, systems, spinal constructs, implants and methods are disclosed.

In some embodiments, a surgical system is provided. The surgical system includes a fastener comprising a first end including a socket and a second end configured to penetrate tissue. A first member is engageable with the socket. A second member includes a collet configured for capturing the first end. A third member is engageable with the collet to releasably capture the fastener. An actuator is connected with the second member and the third member. The actuator includes a knob having a threaded inner surface and a threaded coupling member engageable with the threaded inner surface to actuate axial translation of the second member relative to the third member.

In some embodiments, the surgical system includes a bone fastener comprising a spherical head including a socket and a threaded second end configured to penetrate tissue. A driver member is engageable with the socket. A first sleeve includes a collet configured for capturing the fastener. A second sleeve is engageable with the collet to releasably capture the head. An actuator is connected with the second member and the third member. The actuator includes a knob having a threaded inner surface and a coupling member having a threaded portion engageable with the threaded inner surface to actuate axial translation of the second member relative to the third member.

BRIEF DESCRIPTION OF THE DRAWINGS

The present disclosure will become more readily apparent from the specific description accompanied by the following drawings, in which:

FIG. 11 is a break away cross section view of components of the surgical system shown in FIG. 1;

FIG. 12 is an axial cross section view of the components shown in FIG. 11 taken along the lines XII-XII;

DETAILED DESCRIPTION

Figure 1:
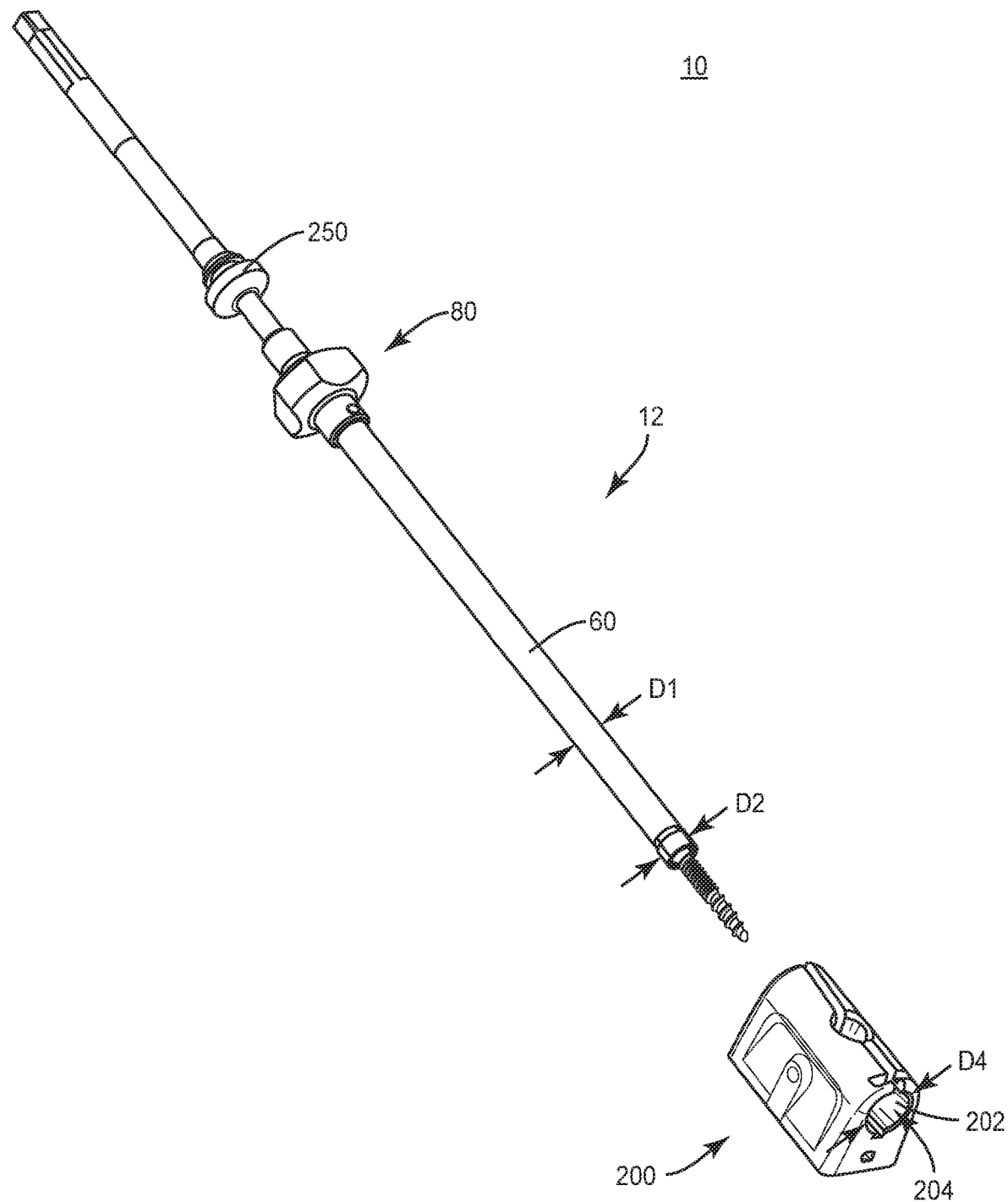
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes a surgical instrument that comprises a screw driver configured for use with robotic guidance. In some embodiments, the screw driver is configured for use with a spinal implant, for example, a bone fastener. In some embodiments, the screw driver includes an outer diameter of about 8.96 mm. In some embodiments, the screw driver is configured for insertion through an end effector having an inner diameter of about 9.0 mm. The configuration of the screw driver avoids using an instrument with an incorrectly sized arm guide that may affect accuracy.

In some embodiments, the present surgical system includes a surgical instrument that comprises a screw driver having an inner shaft, an inner sleeve and an outer sleeve. In some embodiments, the screw driver has an inner sleeve with a flexible collet. In some embodiments, the flexible collet is configured to snap around a spherical head of a bone fastener. In some embodiments, the inner sleeve includes an engagement surface, for example, a tapered surface, configured for slidable engagement with the outer sleeve to lock the collet around a head of a bone screw. In some embodiments, the outer sleeve compresses the engagement surface and the collet to reduce an outer diameter of the collet. In some embodiments, this configuration allows the screw driver to maintain an outer diameter of about 8.96 mm.

In some embodiments, the present surgical system includes a surgical instrument that comprises a screw driver having an actuator. In some embodiments, the actuator includes a knob and a coupling member. In some embodiments, the coupling member includes external threads configured to engage internal threads on the knob. In some embodiments, the coupling member is configured to engage the inner sleeve with pins. In some embodiments, the coupling member is threaded forward to retract the outer sleeve from the taper of the inner sleeve, which allows the collet to open. In some embodiments, the actuator is configured to slide and translate back and forth freely. In some embodiments, the inner shaft is keyed with the inner sleeve to resist and/or prevent relative rotation. In some embodiments, the present surgical system includes a surgical instrument that comprises a screw driver having a collet that expands and snaps over a bone screw head. In some embodiments, the actuator causes the outer sleeve to translate along the engagement surface to snap the collet onto the head of the bone screw.

In some embodiments, the present surgical system includes a surgical instrument that comprises a screw driver having an actuator with a knob and a coupling member such that rotating the knob draws the inner sleeve back axially to clamp on the bottom of the bone screw. As such, the outer sleeve clamps on a taper of the collet to fix the collet with the head of the bone fastener. In some embodiments, the outer sleeve is keyed to the inner sleeve. In some embodiments, the inner sleeve is configured to draw the bone fastener into engagement with the driver. In some embodiments, the head is drawn tight against a shoulder of a hexalobular drive on the inner shaft.

In some embodiments, the present surgical system includes a surgical instrument that comprises a screw driver having an inner shaft with datum surfaces configured to mate with a navigation component and are detectable by image guidance to calculate a position of the navigation component. In some embodiments, the screw driver is configured to connect the navigation component with the screw driver. In some embodiments, the present surgical system includes a bushing that connects the navigation component with the screw driver. In some embodiments, the bushing is assembled from the distal end of the inner shaft to prevent damaging the datum surfaces.

In some embodiments, the present surgical system includes a method of assembling components of a screw driver including the step of attaching the bushing with an inner shaft. In some embodiments, the method includes the step of inserting a distal end of the inner shaft into an opening of the bushing and the bushing is translated and selectively disposed adjacent at least one datum surface. In some embodiments, the present surgical system includes a method of assembling components of a screw driver including the step of attaching a key into a slot of the inner shaft; attaching the knob to the inner shaft by translating the knob from the distal end of the inner shaft; and inserting a retaining ring to connect the knob with the inner shaft. In some embodiments, the method includes the steps of inserting the distal end of the inner shaft into the outer sleeve and translating the outer sleeve along the inner shaft into engagement with the knob; attaching the inner sleeve by inserting the inner sleeve into a channel of the outer sleeve and translating the inner sleeve into alignment with the key; attaching the coupling member by translating the coupling member along the outer sleeve into a threaded engagement with the knob; and inserting pins to connect the coupling member with the inner and outer sleeves and welding the pins. See, for example, the embodiments and disclosure of systems and methods of assembling components of a screw driver, shown and described in commonly owned and assigned U.S. patent application Ser. No. 16/564,599 filed Sep. 9, 2019, the entire contents of which being incorporated herein by reference.

In some embodiments, the present surgical system comprises a surgical instrument that comprises a screw driver that can be employed with bone fasteners and one or more implant supports for treating a spine. In some embodiments, the present surgical system includes a surgical instrument that can easily connect and disconnect from a bone fastener. In some embodiments, the present surgical system includes a surgical instrument that can be employed with an end effector of a robotic arm to facilitate implantation with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of a spinal implant system 10, in accordance with the principles of the present disclosure.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 26:
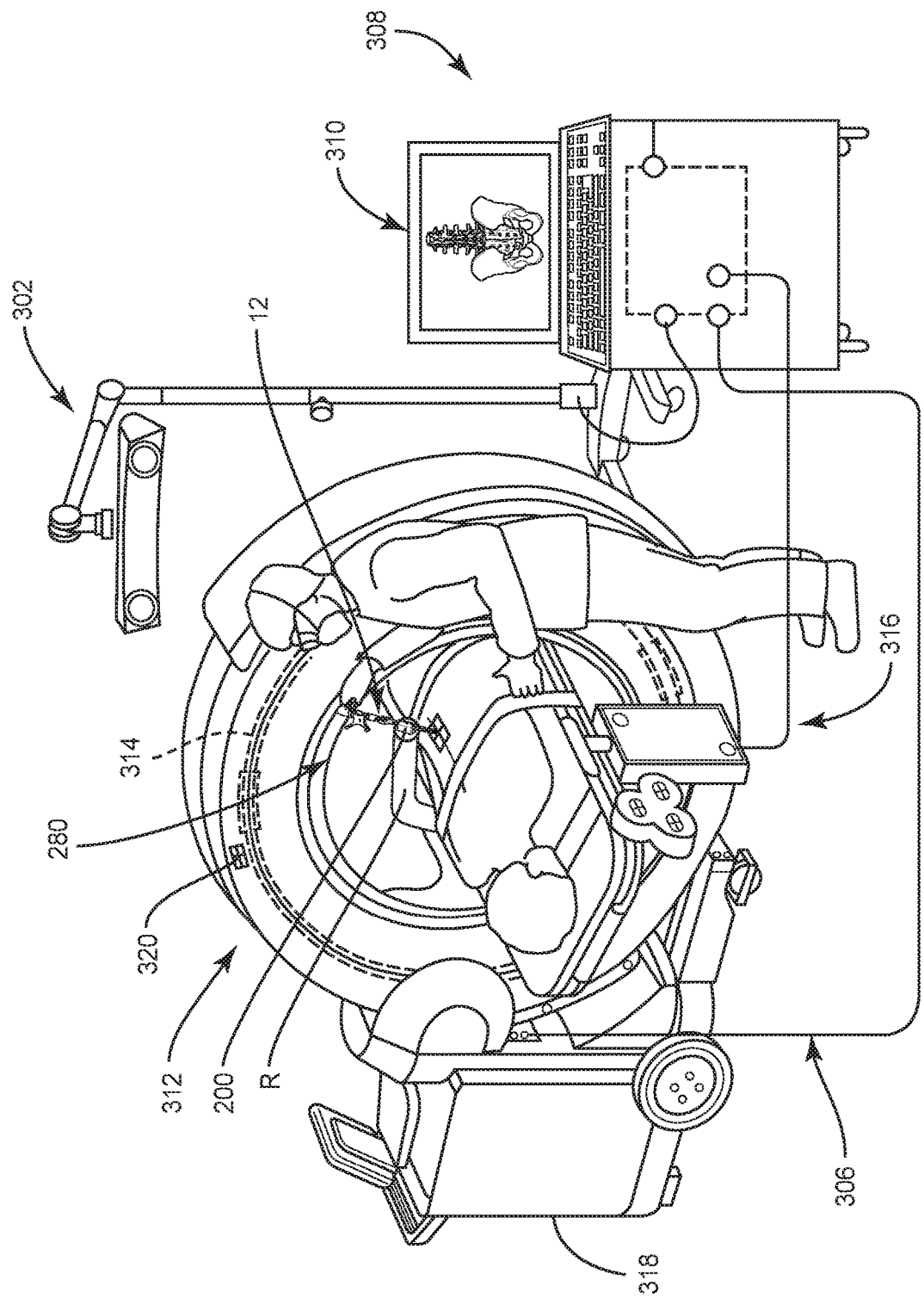
FIG. 26 is a perspective view of components of one embodiment of a surgical system in accordance with the principles of the present disclosure.

Spinal implant system 10 includes a surgical instrument, such as, for example, a surgical driver 12. Surgical driver 12 can be employed with an end effector 200, as shown in FIG. 1, to facilitate implantation with a robotic arm R (FIG. 26). Surgical driver 12 is guided through end effector 200 for guide-wireless insertion of a spinal implant, for example, a bone fastener 100, as described herein.

Figure 2:
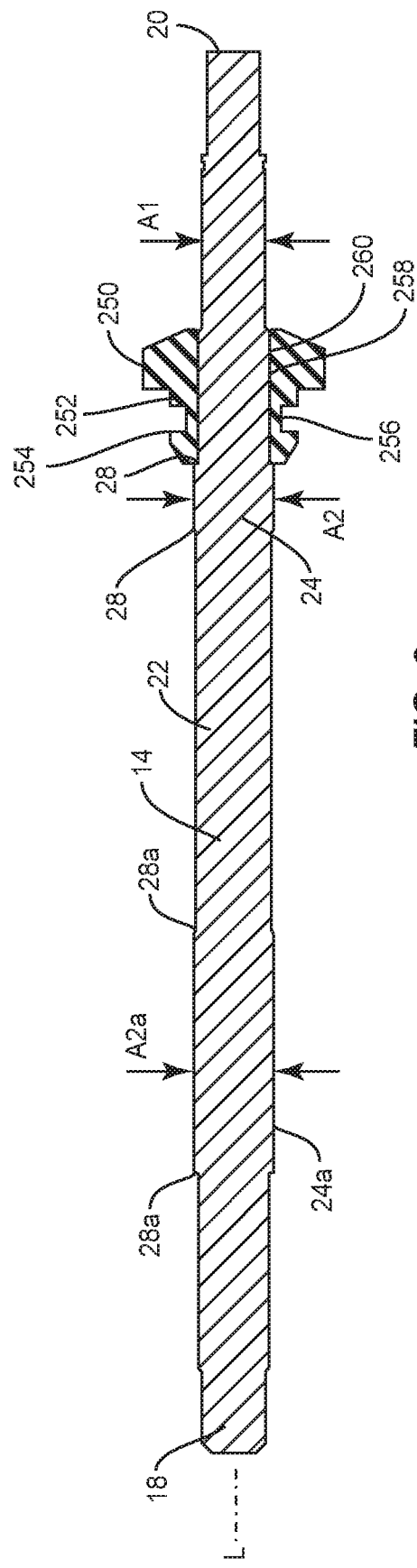
FIG. 2 is a side, cross-section view of components of the surgical system shown in FIG. 1.
Figure 3:
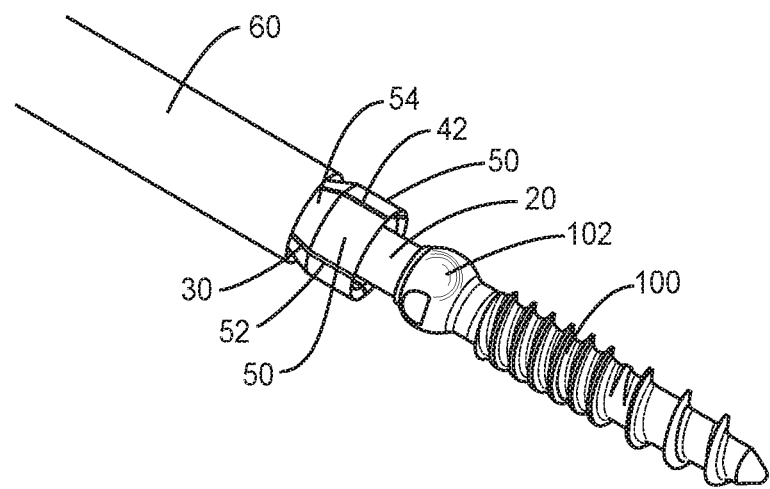
FIG. 3 is a break away view of components of the surgical system shown in FIG. 1.
Figure 4:
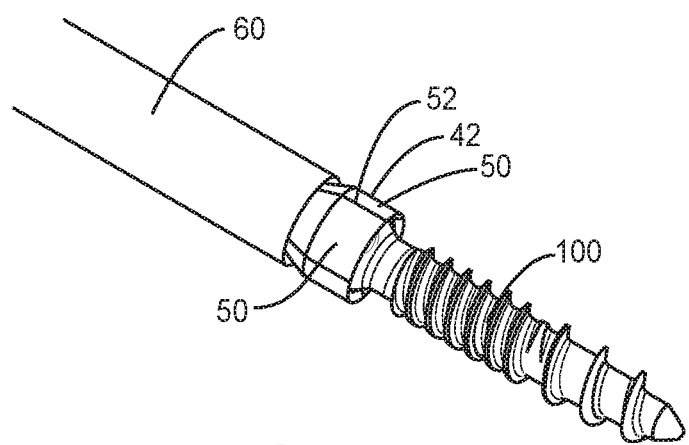
FIG. 4 is a break away view of components of the surgical system shown in FIG. 1.
Figure 5:
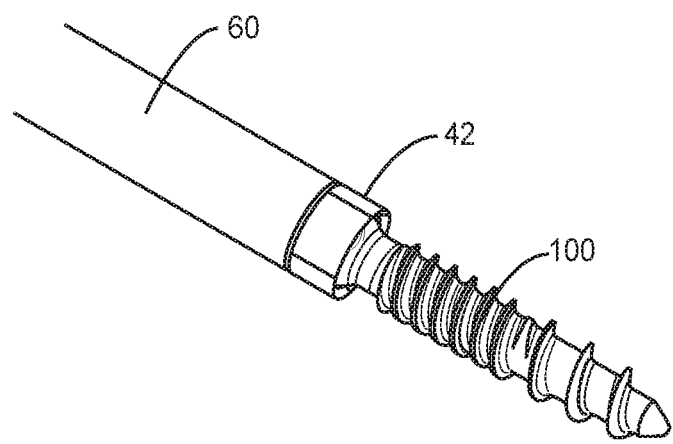
FIG. 5 is a break away view of components of the surgical system shown in FIG. 1.

Surgical driver 12 includes a member, for example, a driver shaft 14 extending along an axis L between a proximal end 18 and a distal end 20, as shown FIG. 2. End 20 is configured for engagement with an implant, for example, a bone fastener 100, as shown in FIG. 3. In some embodiments, end 20 may have different cross-sections such as square, hexagonal, polygonal, triangular, star or hexalobe. End 20 may have various surface configurations, for example, smooth, rough, arcuate, undulating, porous, semi-porous, dimpled, polished and/or textured. Shaft 14 includes a slot 114 configured for disposal of a part, for example, a key 116. Key 116 is configured to connect shaft 14 with a member, as described herein, to resist and/or prevent relative rotation.

Shaft 14 includes an outer surface 22. Surface 22 includes one or more datum surfaces 24, 24a. Surface 24 is disposed on shaft 14 a selected distance from distal end 20. Surface 24 is detectable by image guidance and utilized to calculate a position of a navigation component 280, as described herein, surgical driver 12 and/or bone fastener 100 during a surgical procedure. Surface 24 is configured for connection with a portion of navigation component 280 to facilitate positioning and/or tracking of navigation component 280, surgical driver 12 and/or bone fastener 100 during a surgical procedure. Shaft 14 includes a diameter A1 and surface 24 include a diameter A2. In some embodiments, diameter A2 is greater than diameter A1 such that surface 24 forms an edge 28, as shown in FIG. 2. Edge 28 is configured to provide a stop for a part, for example, a bushing 250 during assembly, as described herein. Bushing 250 is configured to connect navigation component 280 with surgical driver 12. Bushing 250 includes a flange 252 and a flange 254 that is spaced apart from flange 252. Bushing 250 includes a recess 256 between flanges 252, 254. Bushing 250 includes an inner surface 258 that defines an opening 260.

Surface 24a is disposed on shaft 14 a selected distance from distal end 20. Surface 24a is detectable by image guidance and utilized to calculate a position of a navigation component 280, as described herein, surgical driver 12 and/or bone fastener 100 during a surgical procedure. Surface 24a is configured for connection with a portion of navigation component 280 to facilitate positioning and/or tracking of navigation component 280, surgical driver 12 and/or bone fastener 100 during a surgical procedure. Surface 24a includes a diameter A2a. In some embodiments, diameter A2a is greater than diameter A1 such that surface 24a forms an edge 28a, as shown in FIG. 2.

A member, for example, a sleeve 30 is configured for disposal of shaft 14. Sleeve 30 extends between an end 32 and an end 34 along axis L. Sleeve 30 includes an inner surface 36 and an outer surface 38. Surface 36 defines a passageway 40 coaxial with axis L and configured for disposal of shaft 14. Surface 36 includes an opening 37 configured for disposal of key 116 for a keyed connection between shaft 14 and sleeve 30, as shown in FIG. 12. Connection of shaft 14 with sleeve 30 allows for axial translation of shaft 14 and sleeve 30 thereby preventing and/or resisting relative rotation. Surface 38 includes an opening 39 configured for alignment with a member, for example, a sleeve 60 to facilitate relative axial translation, as described herein.

Figure 6:
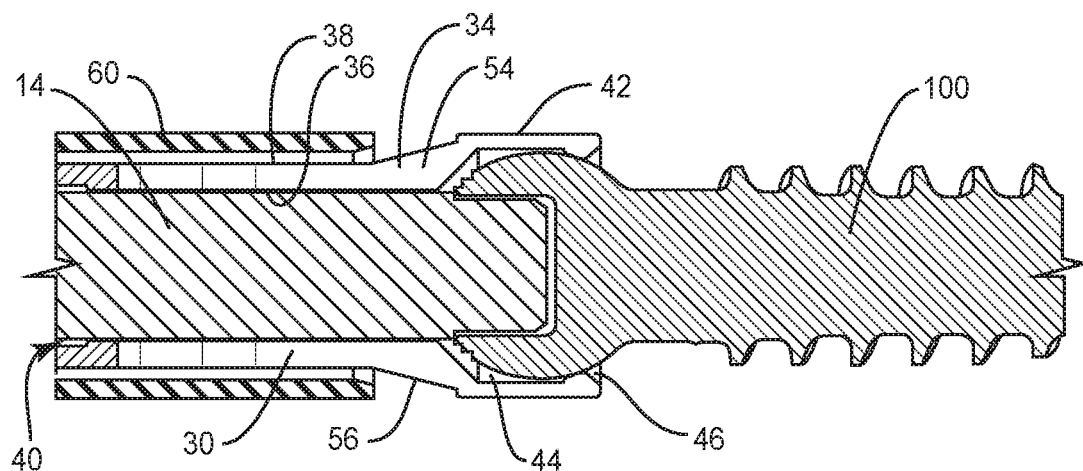
FIG. 6 is a cross section view of the components shown in FIG. 5.
Figure 7:
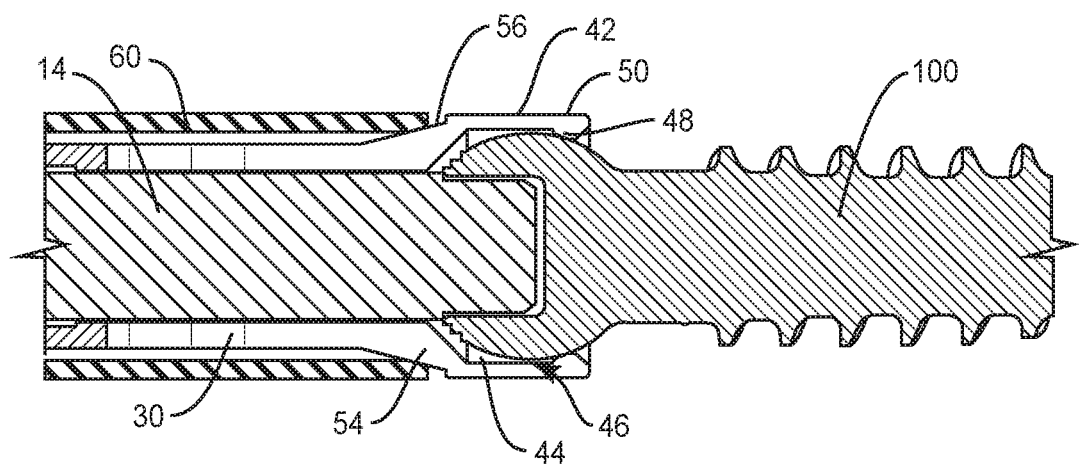
FIG. 7 is a cross section view of the components shown in FIG. 4.

End 34 includes an expandable member, for example, a collet 42. Collet 42 extends from end 34 and is configured for movement between a first configuration and a second configuration, as described herein. Collet 42 comprises an inner surface 44 defining a passageway 46, as shown in FIGS. 6 and 7. Passageway 46 is coaxial with passageway 40. Passageway 46 has a cylindrical cross-section configuration. In some embodiments, passageway 46 may have various cross section configurations, such as, for example, oval, oblong, triangular, rectangular, square, polygonal, irregular, uniform, non-uniform, variable, tubular and/or tapered.

Collet 42 includes a locking surface 48 defined by a plurality of cantilevered fingers 50 extending radially outward. Fingers 50 are circumferentially disposed and are equidistantly spaced apart. Fingers 50 are spaced apart by a gap 52. In one embodiment, collet 42 is flexible such that collet 42 is biased to the closed position, as described herein, for a provisional lock between collet 42 and bone fastener 100. Collet 42 is configured to snap fit around an end, for example, a head 102 of bone fastener 100. As collet 42 translates over head 102 of bone fastener 100, collet 42 moves from a closed position to an open position and back to the closed position to provisionally capture head 102.

End 34 of sleeve 30 includes an engagement surface 54 disposed proximal to collet 42. Surface 54 is configured for translation of a member, for example, a sleeve 60, as described herein. Surface 54 includes a tapered configuration that defines a ramp 56. Ramp 56 includes an inclined configuration from end 34 to collet 42. Sleeve 60 is configured to slidably engage surface 54 to lock collet 42, as described herein.

Sleeve 60 extends between a proximal end 62 and a distal end 64 along axis L. Sleeve 60 includes an inner surface 66 and an outer surface 68. Surface 66 defines a passageway 70 coaxial with axis L and configured for moveable disposal of sleeve 30. In one embodiment, inner surface 66 may have various surface configurations to enhance engagement with sleeve 30 and/or collet 42, for example, rough, arcuate, undulating, porous, semi-porous, dimpled, polished and/or textured.

Figure 8:
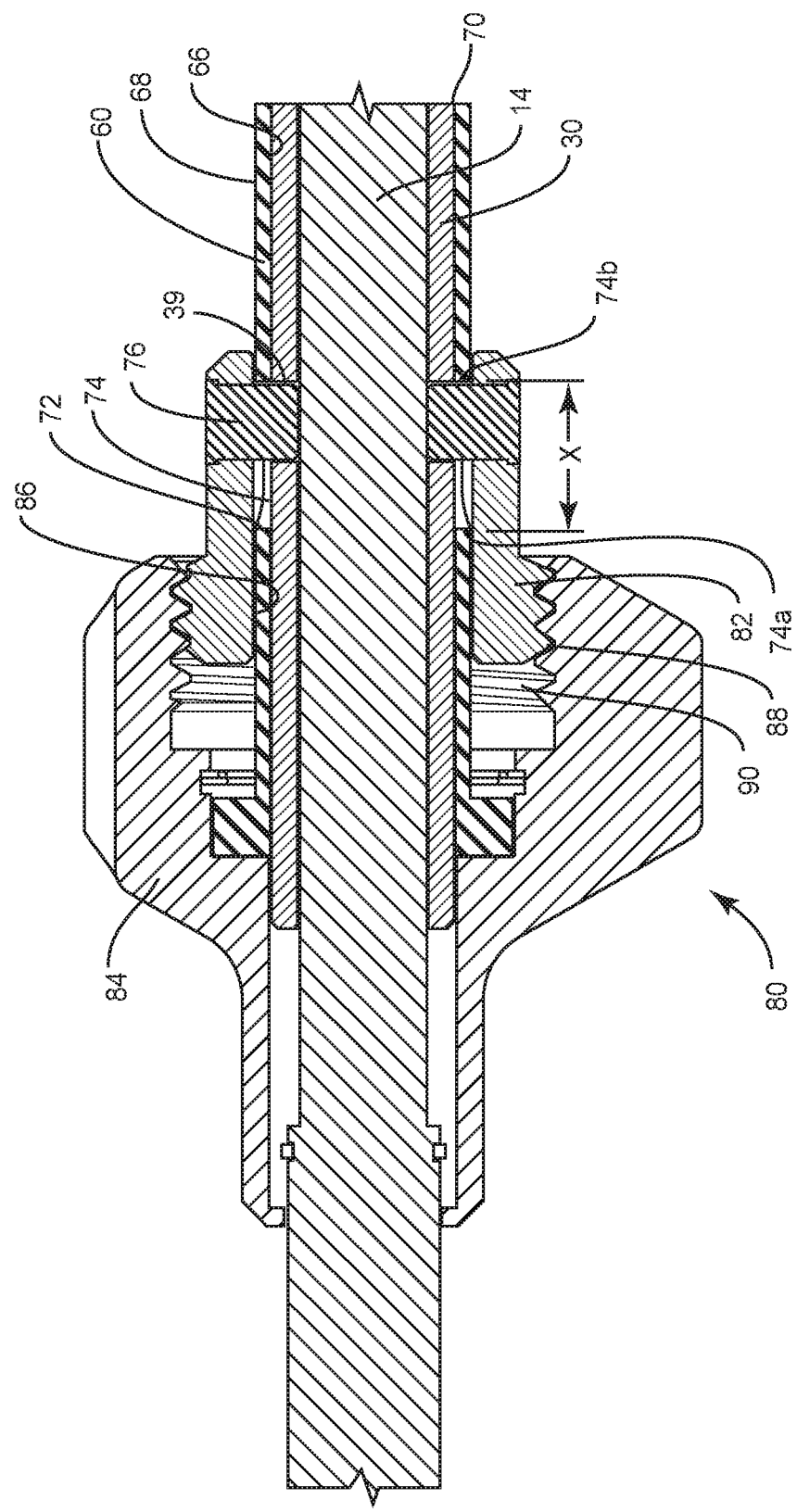
FIG. 8 is a break away cross section view of components of the surgical system shown in FIG. 1.

End 62 includes a surface 72 that defines an elongated slot 74 configured for disposal of a pin 76, as shown in FIG. 8. Pin 76 is disposed with opening 39 and slot 74 to facilitate relative axial translation. Slot 74 extends a distance x along a portion of sleeve 60 between an end 74a and an end 74b.

Sleeve 60 is configured to lock collet 42 with head 102, as discussed herein, for releasable fixation with bone fastener 100. End 64 is slidably engageable with surface 54. Surface 54 is moveably positioned within passageway 70 to move between a configuration in which surface 54 is spaced apart from passageway 70 and a configuration in which surface 54 is positioned within passageway 70 for disposal adjacent collet 42 to lock collet 42. As end 64 axially translates along surface 54, fingers 50 are driven further inwardly by the force of sleeve 60 engaging surface 54 such that fingers 50 are moveable to the locked position around head 102.

Figure 9:
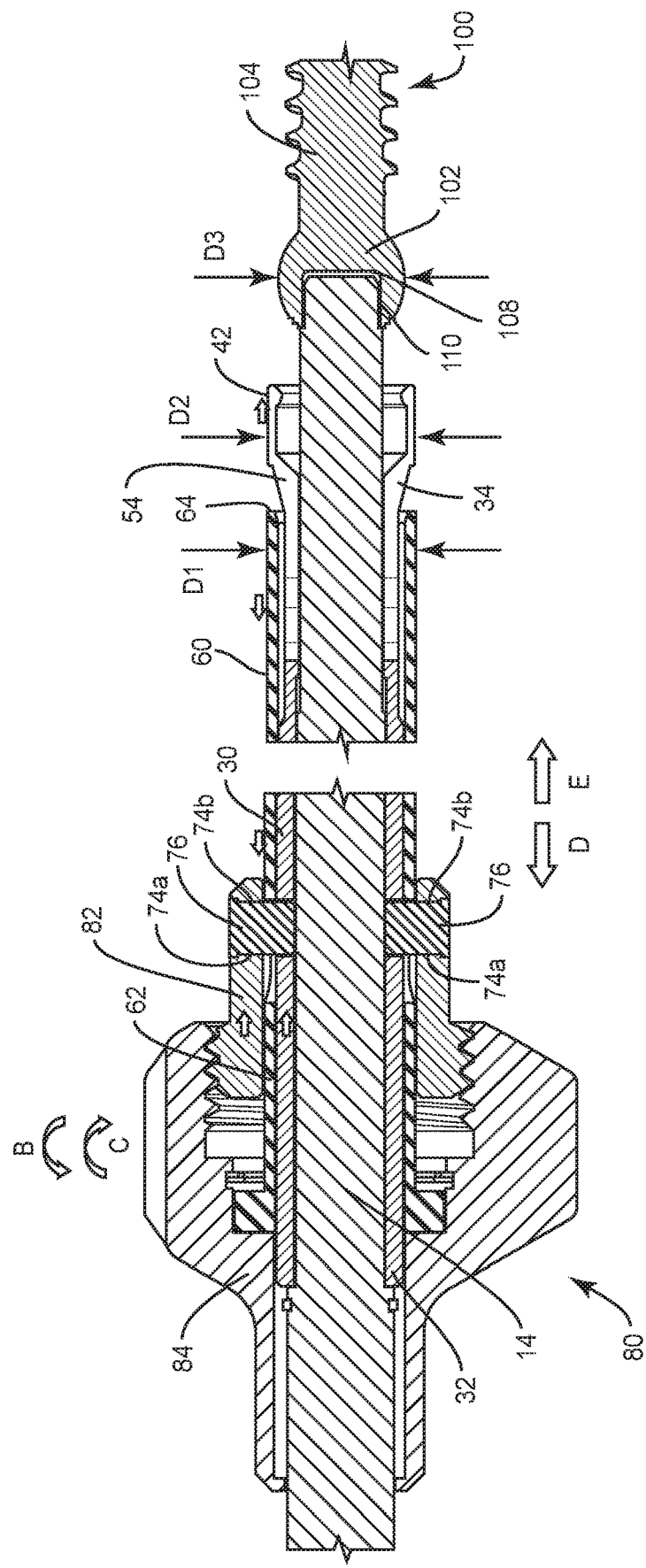
FIG. 9 is a break away cross section view of components of the surgical system shown in FIG. 1.
Figure 10:
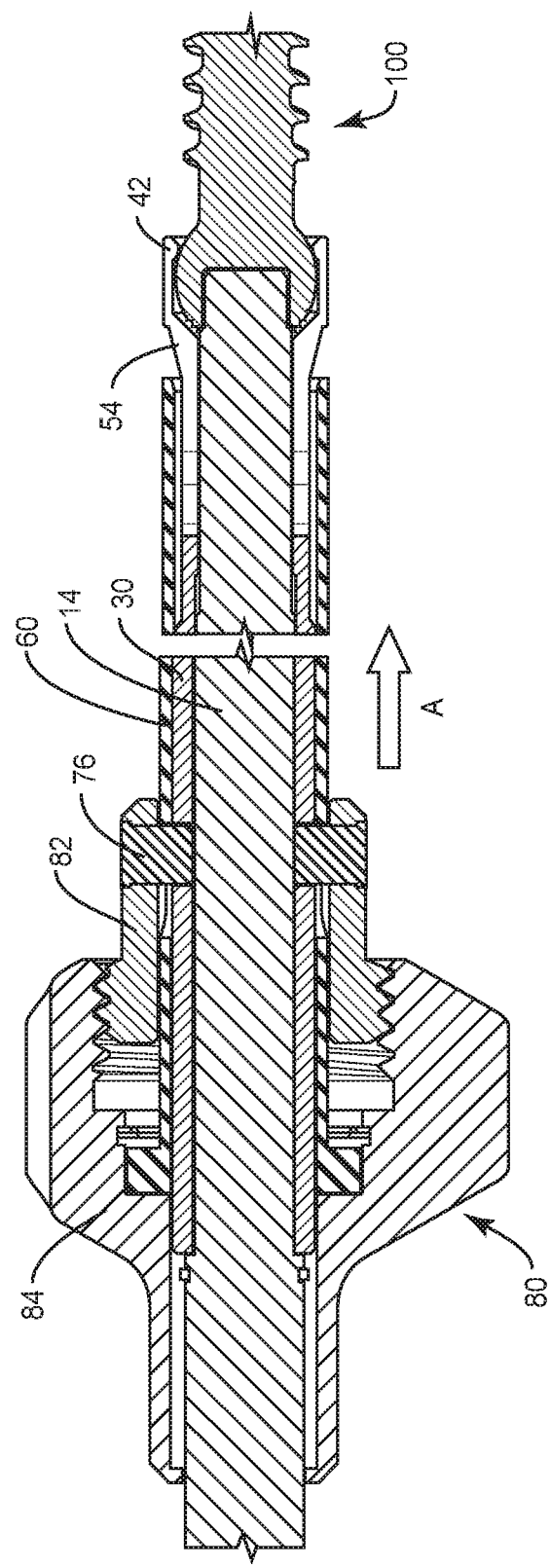
FIG. 10 is a break away cross section view of components of the surgical system shown in FIG. 1.
Figure 13:
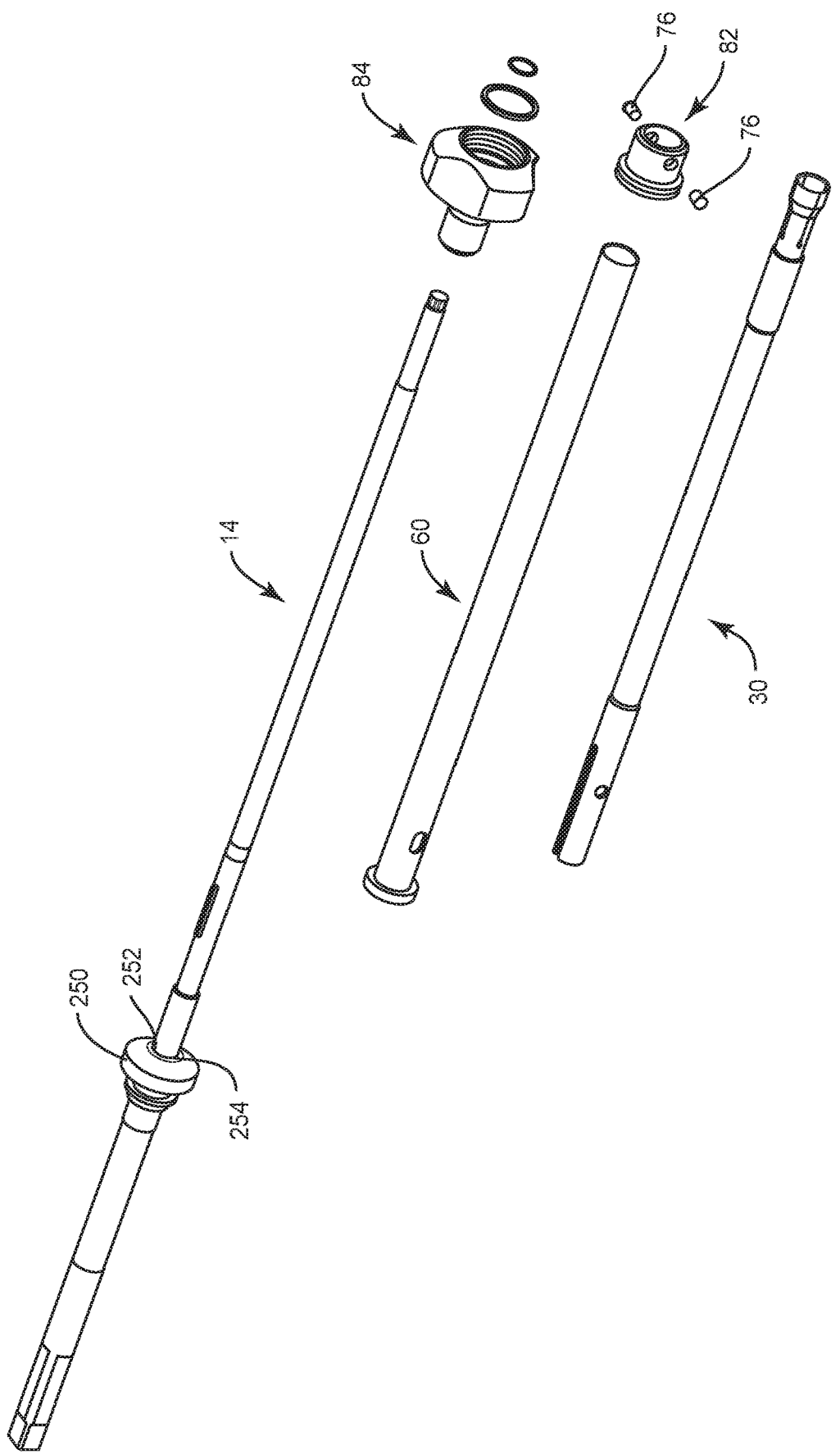
FIG. 13 is a perspective view of components of one embodiment of a surgical system in accordance with the principles of the present disclosure with parts separated.

Sleeve 60 includes a diameter D1 and collet 42 includes a diameter D2. Diameter D1 is about 8.0 to about 8.99 mm to facilitate insertion through end effector 200 having an inner diameter D4 of about 8.5 mm to about 10.0 mm. Diameters D1, D2 are slightly larger than a proximal end diameter D3 of bone fastener 100, as shown in FIG. 9. As sleeve 60 translates over surface 54, sleeve 60 compresses collet 42 to decrease diameter D2 to about diameter D1. This configuration allows bone fastener 100 and surgical driver 12 to pass through end effector 200, as described herein.

Surgical driver 12 includes an actuator 80 connected with sleeve 30 and sleeve 60. Actuator 80 includes a coupling member 82 and a knob 84. Coupling member 82 includes an inner surface 86. Surface 86 includes one or more pins 76 extending therefrom to connect actuator 80 with sleeves 30, 60, as described herein. Coupling member 82 includes a threaded portion 88. Knob 84 includes a threaded inner surface 90 configured to rotatably engage threaded portion 88 for axial translation of sleeve 30 relative to sleeve 60, which causes releasable locking of collet 42 with bone fastener 100, as discussed herein.

Actuator 80 is engaged to cause relative translation of sleeves 30, 60. For example, to fix surgical driver 12 with bone fastener 100, knob 84 is rotated in a clockwise direction, as shown by arrow B in FIG. 9. Rotation of knob 84 in the clockwise direction causes translation of coupling member 82, in a direction shown by arrow E in FIG. 9. Connection of coupling member 82 and sleeve 30 by pins 76 causes sleeve 30 to simultaneously translate, in the direction shown by arrow E in FIG. 9. As pins 76 approach ends 74b, pins 76 cause sleeve 60 to translate, in the direction shown by arrow E in FIG. 9, such that distal end 64 slidably engages surface 54 and surface 54 is positioned within passageway 70 for disposal adjacent collet 42 to lock collet 42, as described herein.

To disengage surgical driver 12 from bone fastener 100, knob 84 is rotated in a counter-clockwise direction, as shown by arrow C in FIG. 9, causing translation of coupling member 82, in a direction shown by arrow D in FIG. 9. Connection of coupling member 82 and sleeve 30 by pins 76 causes sleeve 30 to simultaneously translate, in the direction shown by arrow D in FIG. 9. As pins 76 approach ends 74a, pins 76 cause sleeve 60 to translate, in the direction shown by arrow D in FIG. 9, such that distal end 64 slidably disengages from surface 54 and surface 54 is spaced apart from passageway 70 to release collet 42, as described herein.

Bone fastener 100 includes a head 102 configured for engagement with shaft 14 and an elongated shaft 104 configured for penetrating tissue. Head 102 comprises a spherical configuration. Head 102 includes an outer circumferential surface having a substantially spherical configuration. Head 102 includes an inner surface 108 that defines a cavity, for example, a mating surface 110. Mating surface 110 is configured for disposal of an instrument and/or tool extension, for example, end 20 of shaft 14, as discussed herein. Mating surface 110 is centrally positioned with respect to head 102. Mating surface 110 is coaxial with axis L. In some embodiments, mating surface 110 may have various cross-section configurations, for example, oval, oblong, triangular, rectangular, square, polygonal, irregular, uniform, non-uniform, variable, tubular and/or tapered. In some embodiments, inner surface 108 may have various surface configurations, for example, smooth and/or surface configurations to enhance engagement with the mating surface of shaft 14, for example, rough, arcuate, undulating, porous, semi-porous, dimpled, polished and/or textured.

Shaft 104 has a cylindrical cross section configuration and includes an outer surface having an external thread form. In some embodiments, the thread form may include a single thread turn or a plurality of discrete threads. In some embodiments, other engaging structures may be disposed on shaft 104, for example, a nail configuration, barbs, expanding elements, raised elements and/or spikes to facilitate engagement of shaft 104 with tissue, for example, vertebrae.

In some embodiments, all or only a portion of shaft 104 may have alternate cross section configurations, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue for example, rough, arcuate, undulating, mesh, porous, semi-porous, dimpled and/or textured. In some embodiments, all or only a portion of shaft 104 may be disposed at alternate orientations, relative to a longitudinal axis of bone fastener 100, for example, transverse, perpendicular and/or other angular orientations such as acute or obtuse, co-axial and/or may be offset or staggered. In some embodiments, all or only a portion of shaft 104 may be cannulated.

Figure 14:
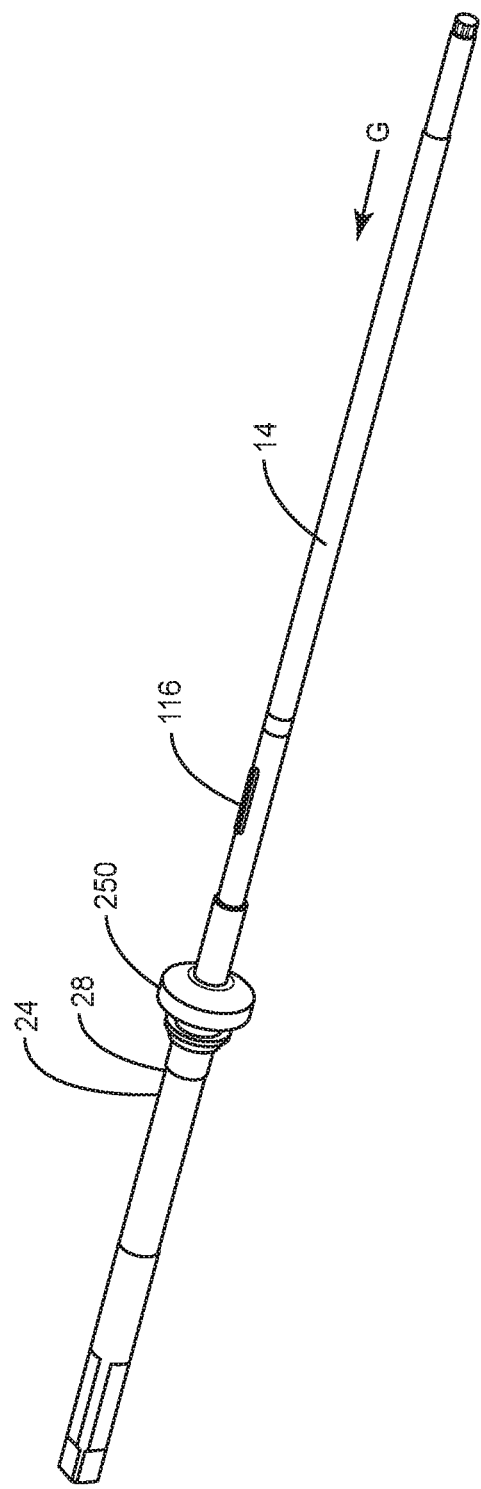
FIG. 14 is a perspective view of components of one embodiment of a surgical system in accordance with the principles of the present disclosure.
Figure 15:
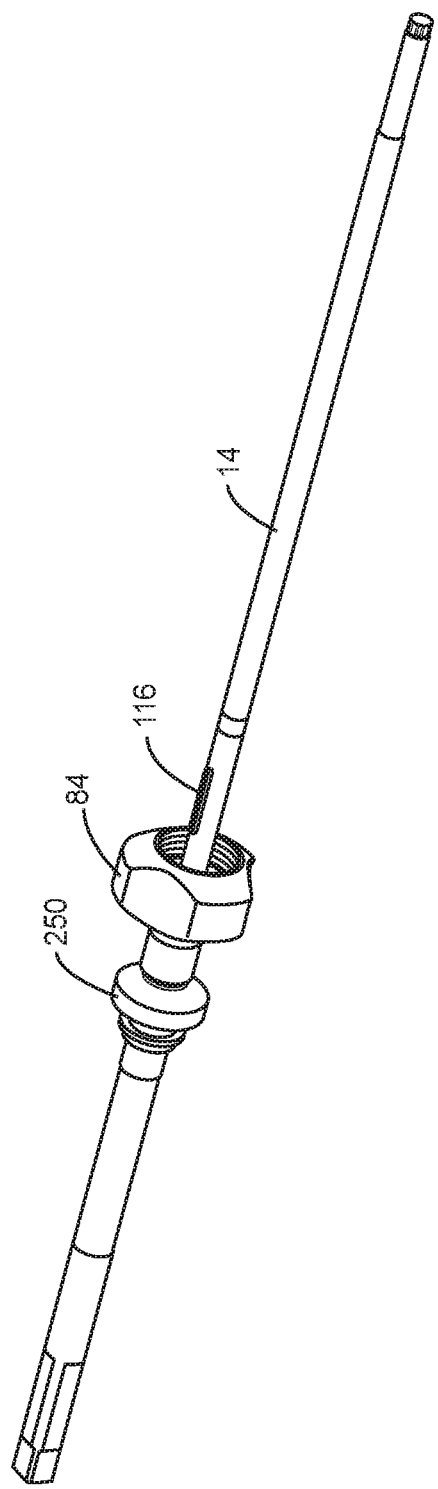
FIG. 15 is a perspective view of components of one embodiment of a surgical system in accordance with the principles of the present disclosure.
Figure 16:
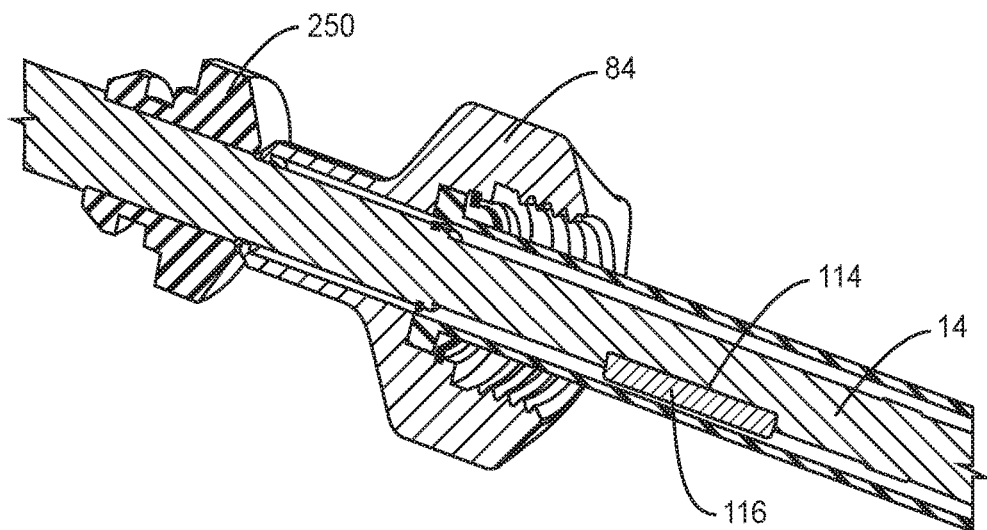
FIG. 16 is a break away, cross section view of components of the surgical system shown in FIG. 15.
Figure 17:
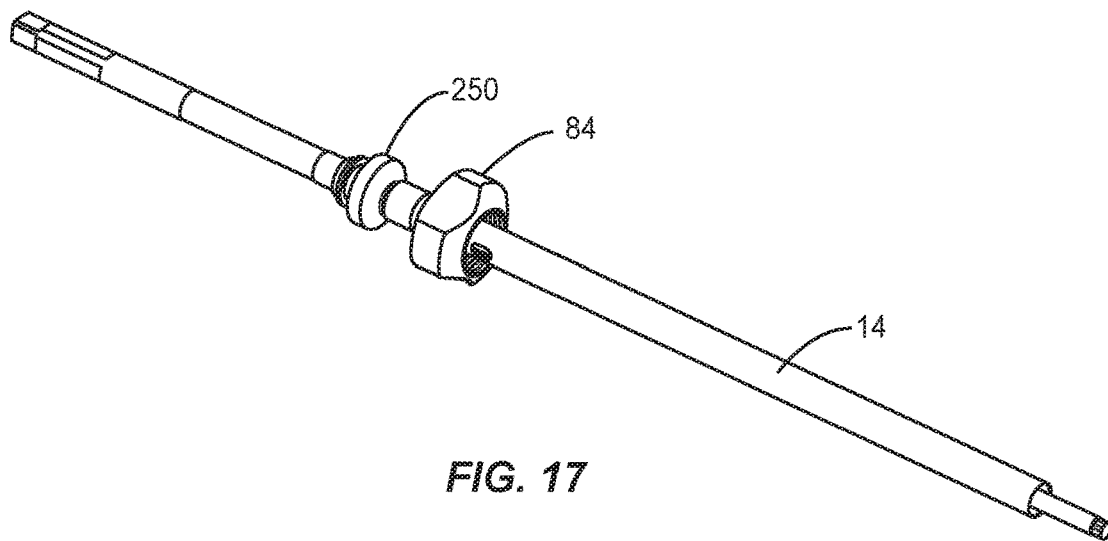
FIG. 17 is a perspective view of components of one embodiment of a surgical system in accordance with the principles of the present disclosure.
Figure 18:
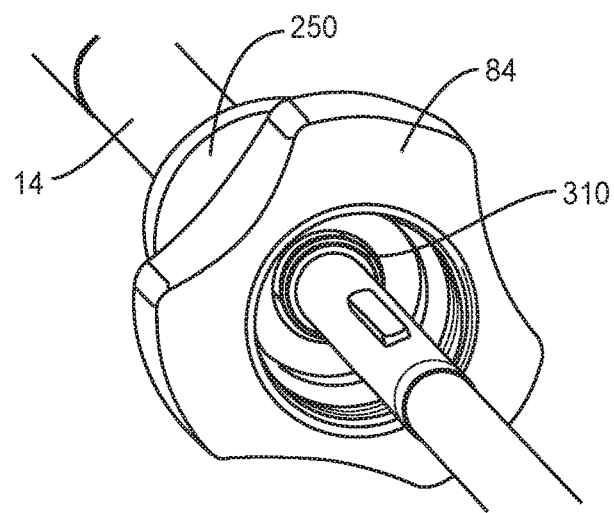
FIG. 18 is a break away view of components of the surgical system shown in FIG. 15.

In some embodiments, spinal implant system 10 includes a method of assembling the components of surgical driver 12, as shown in FIGS. 13-24, which includes the step of attaching bushing 250 with shaft 14. Distal end 20 is inserted into opening 260 such that bushing 250 translates along shaft 14 from distal end 20, in a direction shown by arrow G in FIG. 14. The inner diameter of opening 260 allows relative translation of the portion of shaft 14 having diameter A1, as shown in FIGS. 2 and 14. Bushing 250 is translated into an abutting engagement with edge 28, as shown in FIG. 14. The inner diameter of bushing 250 is less than diameter A2 of surfaces 24 to resist and/or prevent translation of bushing 250 over edge 28 and along surfaces 24. Edge 28 prevents further translation of bushing 250 such that inner surface 258 does not contact surfaces 24, 24a to resist and/or prevent damaging surfaces 24, 24a during assembly. Bushing 250 is selectively disposed adjacent along shaft 14 to facilitate positioning of a navigation component 280 relative to surfaces 24 for image guidance.

Figure 19:
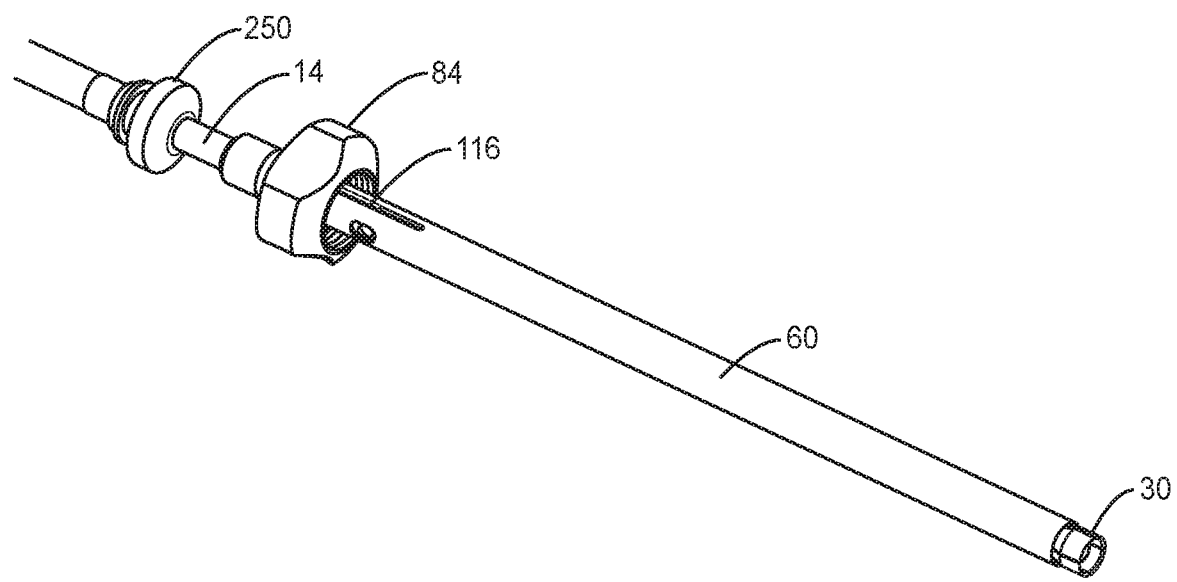
FIG. 19 is a perspective view of components of one embodiment of a surgical system in accordance with the principles of the present disclosure.
Figure 20:
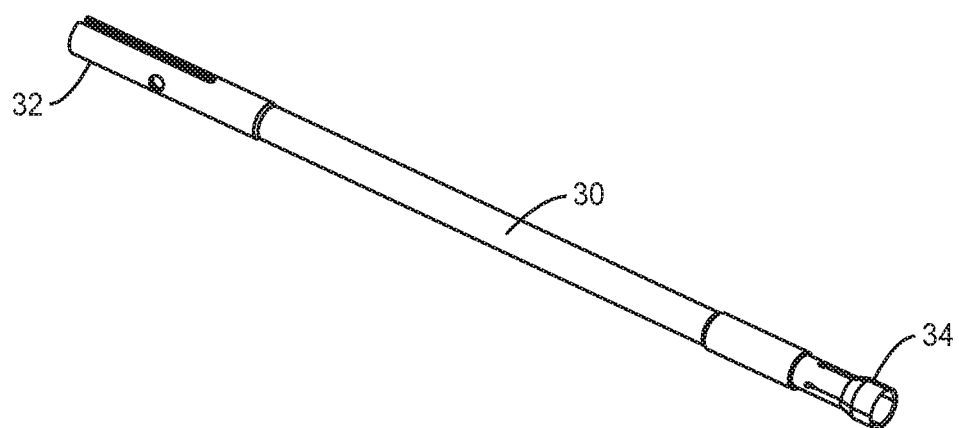
FIG. 20 is a perspective view of components of the surgical system shown in FIG. 19.
Figure 21:
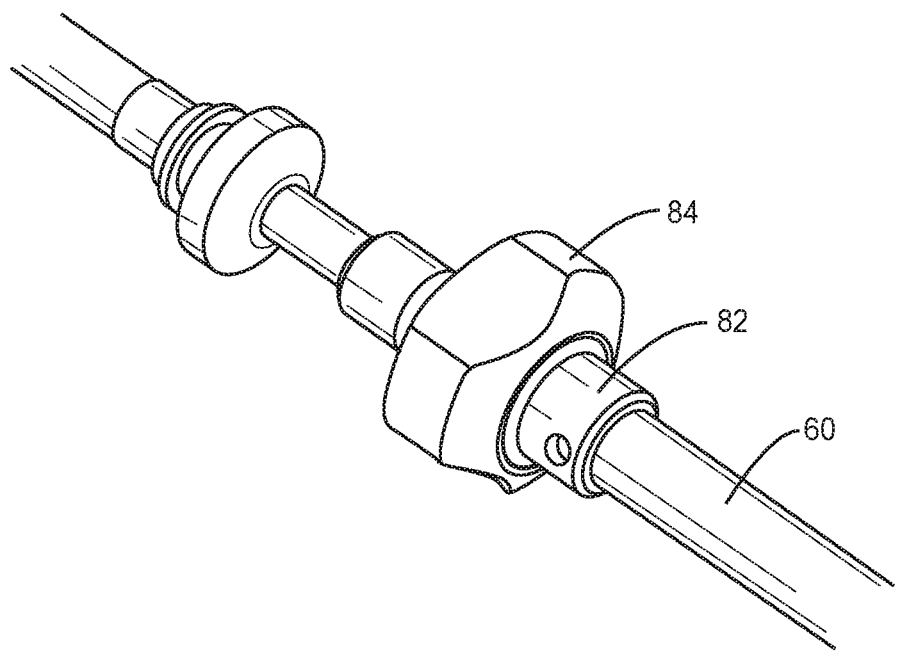
FIG. 21 is a break away view of components of one embodiment of a surgical system in accordance with the principles of the present disclosure.
Figure 22:
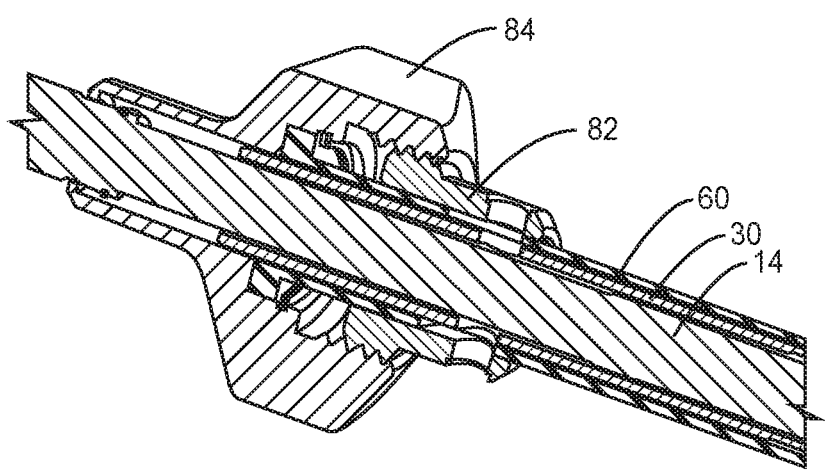
FIG. 22 is a cross section view of the components shown in FIG. 21.
Figure 23:
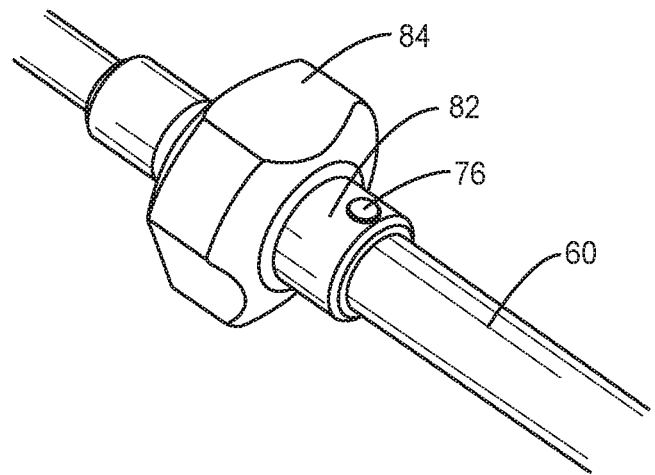
FIG. 23 is a break away view of components of one embodiment of a surgical system in accordance with the principles of the present disclosure.
Figure 24:
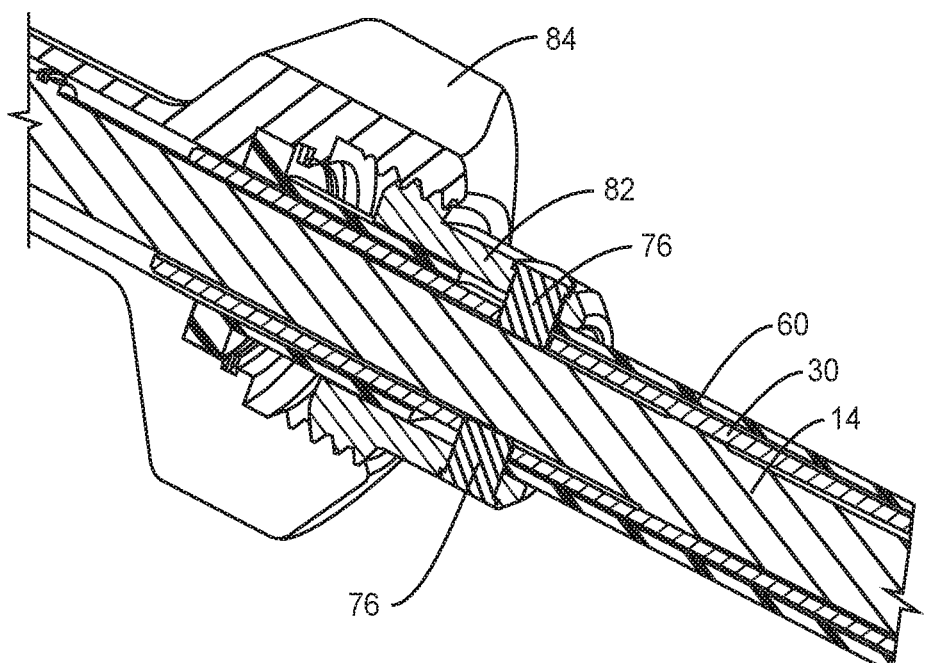
FIG. 24 is a cross section view of the components shown in FIG. 23.

Key 116 is inserted into slot 114. Knob 84 is attached by translating knob 84 from distal end 20 for positioning adjacent bushing 250, as shown in FIGS. 15-18. A retaining ring 310 is inserted to connect knob 84 with shaft 14, as shown in in FIG. 17. Sleeve 60 is connected by inserting distal end 20 into passageway 70 and translating sleeve 60 along shaft 14 into engagement with knob 84, as shown in FIG. 19. Sleeve 30 is attached by inserting sleeve 30 into passageway 70 and translating sleeve 30 such that opening 37 is aligned with key 116, as shown in FIG. 20. Coupling member 82 is attached by translating coupling member 82 along sleeve 60 into a threaded engagement with knob 84, as shown in FIGS. 21 and 22. Pins 76 are inserted into openings 39 and slot 74 to connect coupling member 84 with sleeves 30, 60, as shown in FIGS. 23 and 24.

Figure 25:
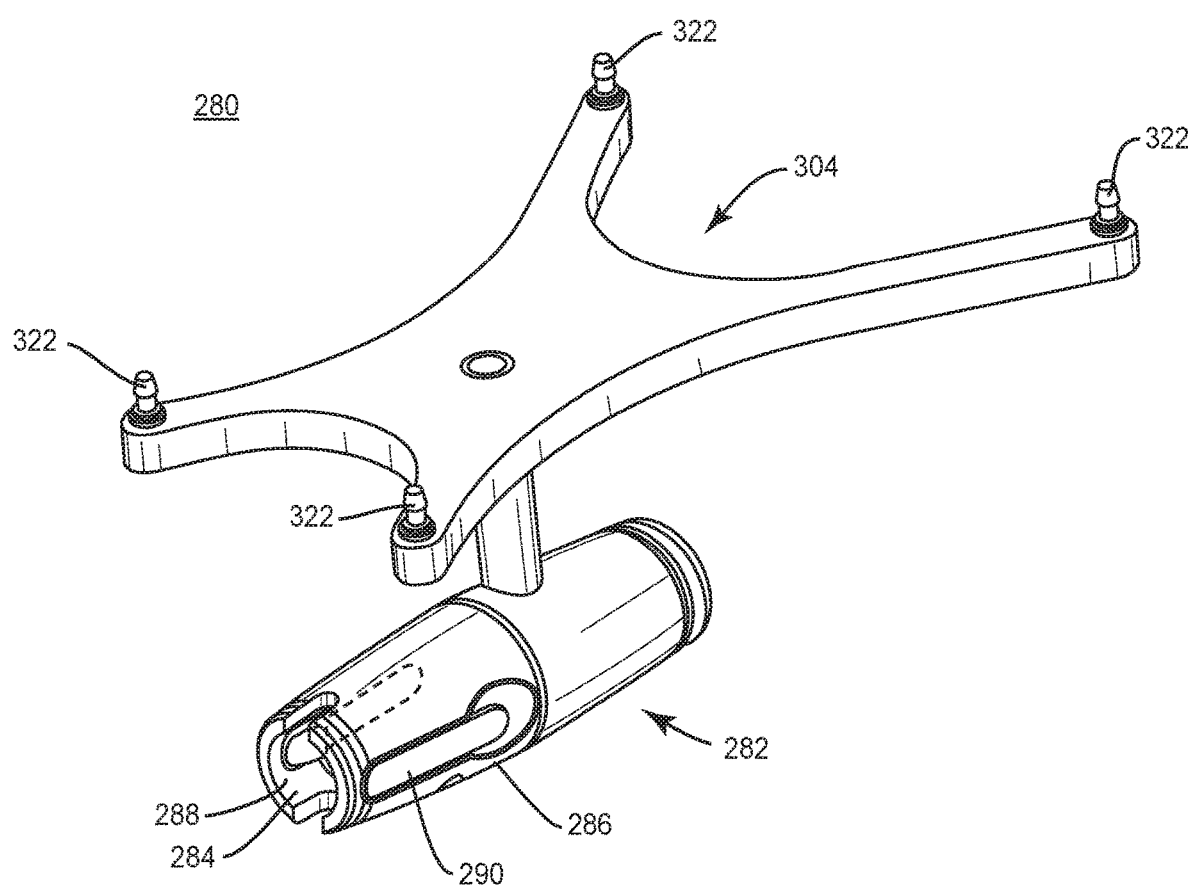
FIG. 25 is a perspective view of components of one embodiment of a surgical system in accordance with the principles of the present disclosure.

Navigation component 280, as shown in FIG. 25, is assembled with surgical driver 12. Navigation component 280 includes a collar 282 having an inner surface 284 and an outer surface 286. Surface 284 defines a passageway 288. Surface 284 is configured for releasable engagement with bushing 250. Passageway 288 is configured to receive shaft 14 and a portion of bushing 250. Collar 282 includes a lock, for example, at least one resilient prong or tab 290. Navigation component 280 is translated from proximal end 18 into a mating engagement with surfaces 24, 24a and connected with bushing 250 by tab 290.

In assembly, operation and use, spinal implant system 10, similar to the systems and methods described herein, is employed with a surgical procedure, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

Navigation component 280 is oriented relative to a sensor array 302, as shown in FIG. 26, to facilitate communication between navigation component 280 and sensor array 302 during a surgical procedure, as described herein. Navigation component 280 is configured to generate a signal representative of a position of bone fastener 100 relative to surgical driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 280 includes an emitter array 304. Emitter array 304 is configured for generating a signal to sensor array 302 of a surgical navigation system 306. In some embodiments, the signal generated by emitter array 304 represents a position of bone fastener 100 relative to surgical driver 12 and relative to tissue, for example, bone. In some embodiments, the signal generated by emitter array 304 represents a three-dimensional position of bone fastener 100 relative to tissue.

In some embodiments, sensor array 302 receives signals from emitter array 304 to provide a three-dimensional spatial position and/or a trajectory of bone fastener 100 relative to surgical driver 12 and/or tissue. Emitter array 304 communicates with a processor of a computer 308 of surgical navigation system 306 to generate data for display of an image on a monitor 310, as described herein. In some embodiments, sensor array 302 receives signals from emitter array 304 to provide a visual representation of a position of bone fastener 100 relative to surgical driver 12 and/or tissue. See, for example, similar surgical navigation components and their use as described in U.S. Pat. Nos. 6,021,343, 6,725,080, and 6,796,988, the entire contents of each of these references being incorporated by reference herein.

Surgical navigation system 306 is configured for acquiring and displaying medical imaging, for example, x-ray images appropriate for a given surgical procedure. In some embodiments, pre-acquired images of a patient are collected. In some embodiments, surgical navigation system 306 can include an O-Arm® imaging device 312 sold by Medtronic Navigation, Inc. having a place of business in Louisville, Colo., USA. Imaging device 312 may have a generally annular gantry housing that encloses an image capturing portion 314.

In some embodiments, image capturing portion 314 may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of surgical navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 320, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, and 5,592,939, the entire contents of each of these references being incorporated by reference herein.

Fluoroscopic images taken are transmitted to a computer 318 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 100 relative to surgical driver 12 and/or tissue can be tracked. Sensor array 302 is located in such a manner to provide a clear line of sight with emitter array 304, as described herein. In some embodiments, fiducial markers 322 of emitter array 304 communicate with sensor array 302 via infrared technology. Sensor array 302 is coupled to computer 308, which may be programmed with software modules that analyze signals transmitted by sensor array 302 to determine the position of each object in a detector space.

Surgical driver 12 is configured for use with a guide member, for example, an end effector 200 of robotic arm R. End effector 200 includes an inner surface 202 that defines a cavity, for example, a channel 204. Channel 204 is configured for passage of bone fastener 100 and disposal of surgical driver 12. Robotic arm R includes position sensors (not shown), similar to those referenced herein, which measure, sample, capture and/or identify positional data points of end effector 200 in three-dimensional space for a guide-wireless insertion of bone fasteners 100 with tissue. In some embodiments, the position sensors of robotic arm R are employed in connection with surgical navigation system 306 to measure, sample, capture and/or identify positional data points of end effector 200 in connection with surgical treatment, as described herein. The position sensors are mounted with robotic arm R and calibrated to measure positional data points of end effector 200 in three-dimensional space, which are communicated to computer 308.

Shaft 14 is aligned with mating surface 110 of bone fastener 100. Collet 42 snap fits around head 102 to provisionally capture head 102. Actuator 80 is rotatable to cause relative translation of sleeves 30, 60. For example, knob 84 is rotated in the clockwise direction causing translation of coupling member 82 and sleeve 60, as described herein. End 64 slidably engages surface 54 to drive fingers 50 inward to the locked position around head 102, as described herein, to fix surgical driver 12 with bone fastener 100. As sleeve 60 translates over surface 54, sleeve 60 compresses collet 42 to decrease diameter D2 to about diameter D1. This configuration allows bone fastener 100 and surgical driver 12 to pass through end effector 200.

Navigation component 280 is oriented relative to sensor array 302, as shown in FIG. 26, to facilitate communication between navigation component 280 and sensor array 302 during the surgical procedure. This configuration provides indicia or display from surgical navigation system 306, as described herein, of components of spinal implant system 10, including bone fastener 100 and surgical driver 12, and their relative positions with tissue in connection with the surgical treatment. Surgical driver 12 is inserted through end effector 200 for insertion to the surgical site.

Bone fastener 100 is implanted at the surgical site and surgical driver 12 is disengaged from bone fastener 100. To disengage surgical driver 12 from bone fastener 100, actuator 80 is rotated in the opposite direction to cause relative translation of sleeves 30, 60 in the opposite direction to disengage collet 42 from head 102. Knob 84 is rotated in a counter-clockwise direction causing translation of coupling member 82, as described herein. Distal end 64 slidably disengages from surface 54 and surface 54 is spaced apart from passageway 70 to release collet 42 from head 102, as described herein. Surgical driver 12 is removed from the surgical site.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, surgical driver 12 is guided to the surgical site via a guidewire, for example, a K-wire (not shown) and/or without the use of an image guide, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member being engageable with a fastener;
   a second member including an expandable portion configured for capturing the fastener, the second member being connected with the first member such that a distal tip of the first member is positioned within the expandable portion;
   a third member being engageable with the expandable portion to releasably capture the fastener; and
   an actuator connected with the second member and the third member, the actuator including a knob and a coupling member rotatably coupled to the knob such that rotation of the knob relative to the coupling member causes axial translation of the second member relative to the third member, the knob and the coupling member each being rotatable relative to the first member.

2. A surgical instrument as recited in claim 1, wherein the expandable portion includes an expandable collet engageable with the fastener.

3. A surgical instrument as recited in claim 1, wherein the expandable portion moves between a first, closed position and to a second, open position with the fastener.

4. A surgical instrument as recited in claim 1, wherein the second member includes a sleeve and an engagement surface disposed between the sleeve and the expandable portion.

5. A surgical instrument as recited in claim 4, wherein the engagement surface includes a tapered configuration.

6. A surgical instrument as recited in claim 4, wherein the engagement surface defines a ramp.

7. A surgical instrument as recited in claim 4, wherein a distal end of the third member is slidably engageable with the engagement surface to lock the expandable portion with the fastener.

8. A surgical instrument as recited in claim 4, wherein the third member includes a passageway, the engagement surface being moveably positioned within the passageway to move between a first configuration in which the engagement surface is spaced apart from the passageway and a second configuration in which the engagement surface is positioned within the passageway.

9. A surgical instrument as recited in claim 1, further comprising a pin connecting the second and third members to facilitate relative axial translation.

10. A surgical instrument as recited in claim 9, wherein the third member includes a slot configured for disposal the pin, the slot extending a distance along the third member to allow for translation of the pin within the slot during translation of the third member relative to the second member.

11. A surgical instrument as recited in claim 1, wherein the first member is connected to the second member to prevent the first member from rotating relative to the second member.

12. A surgical instrument as recited in claim 1, wherein the first member is keyed with the second member to facilitate translation of the second member relative to the first member.

13. A surgical system comprising:
a fastener comprising a first end including a socket and a second end configured to penetrate tissue;
a first member being engageable with the socket;
a second member including a collet configured for capturing the first end, the second member being connected with the first member such that a distal tip of the first member is positioned within the collet and the socket;
a third member being engageable with the collet to releasably capture the fastener; and
an actuator connected with the second member and the third member, the actuator includes a knob and a coupling member rotatably coupled to the knob such that rotation of the knob relative to the coupling member causes axial translation of the second member relative to the third member, the knob and the coupling member each being rotatable relative to the first member.

14. A surgical system comprising:
a bone fastener comprising a spherical head including a socket and a threaded second end configured to penetrate tissue;
a driver member engageable with the socket;
a first sleeve including a collet configured for capturing the fastener, the first sleeve being connected with the driver member such that a distal tip of the driver member is positioned entirely within the collet and the socket;
a second sleeve being engageable with the collet to releasably capture the head; and
an actuator connected with the first sleeve and the second sleeve, the actuator includes a knob and a coupling member rotatably coupled to the knob such that rotation of the knob relative to the coupling member causes axial translation of the first sleeve relative to the second sleeve, the knob and the coupling member each being rotatable relative to the driver member.

15. A surgical instrument as recited in claim 1, wherein the first member includes a first slot and the second member includes a second slot, the instrument comprising a key positioned in the slots to prevent relative rotation between the first member and the second member.

16. A surgical instrument as recited in claim 1, wherein the knob engages the first member via a non-threaded connection.

17. A surgical instrument as recited in claim 1, wherein the coupling member is spaced apart from the first member.

18. A surgical instrument as recited in claim 1, wherein the first member extends through opposite proximal and distal ends of the knob.

19. A surgical instrument as recited in claim 1, wherein the knob is monolithic and a proximal end of the second member is positioned in a cavity of the knob.

20. A surgical instrument as recited in claim 1, wherein a proximal end of the third member directly engages an inner surface of the knob to prevent axial translation of the third member relative to the knob in a proximal direction.

* * * * *